(12) United States Patent
Stefan et al.

(10) Patent No.: US 8,123,780 B2
(45) Date of Patent: Feb. 28, 2012

(54) DISMANTABLE MEDICAL FORCEPS SYSTEM

(75) Inventors: Jochen Stefan, Wald (DE); Uwe Bacher, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 704 days.

(21) Appl. No.: 12/112,094

(22) Filed: Apr. 30, 2008

(65) Prior Publication Data

US 2008/0294192 A1 Nov. 27, 2008

(30) Foreign Application Priority Data

May 4, 2007 (DE) .................. 10 2007 021 658

(51) Int. Cl.
*A61B 17/00* (2006.01)
(52) U.S. Cl. ............ 606/205; 606/206; 606/51; 606/52; 81/418; 81/176.3; 81/119
(58) Field of Classification Search .......... 606/205, 606/51, 52, 108, 167, 174, 206; 600/562, 600/104, 141, 142; 81/418, 176.3, 119; 604/22, 604/23; 403/300, 305, 353
See application file for complete search history.

(56) References Cited

U.S. PATENT DOCUMENTS

| | | | |
|---|---|---|---|
| 5,282,800 A | 2/1994 | Foshee et al. | |
| 5,478,318 A | 12/1995 | Yoon | |
| 5,618,308 A * | 4/1997 | Holmes et al. | 606/205 |
| 5,718,714 A * | 2/1998 | Livneh | 606/205 |
| 6,077,290 A * | 6/2000 | Marini | 606/205 |
| 6,086,606 A * | 7/2000 | Knodel et al. | 606/208 |
| 6,099,537 A * | 8/2000 | Sugai et al. | 606/143 |
| 7,025,775 B2 * | 4/2006 | Gadberry et al. | 606/205 |
| 2004/0230221 A1 * | 11/2004 | Gadberry et al. | 606/205 |
| 2005/0165443 A1 * | 7/2005 | Livneh | 606/205 |

FOREIGN PATENT DOCUMENTS

| | | |
|---|---|---|
| DE | 4104757 A1 | 8/1992 |
| DE | 10038085 A1 | 3/2001 |
| DE | 20118882 U1 | 5/2002 |
| WO | 9214414 A1 | 9/1992 |

OTHER PUBLICATIONS

European Search Report; EP 08 00 8152; Feb. 12, 2010; 8 pages.
German Search Report, Aug. 5, 2005, 4 pages.
Storz Advertising Literature—Company catalogue Storz Karl Storz-Endoskope, Laparoscopy Volume, 5th edition, 2005 pages 72 et seq. (3 pages).

* cited by examiner

*Primary Examiner* — Gary Jackson
*Assistant Examiner* — Katrina Stransky
(74) *Attorney, Agent, or Firm* — St. Onge Steward Johnston & Reens LLC (57) ABSTRACT

The present invention is directed toward a dismantlable medical forceps system having a first grip having a movable grip part, a first force transmission element designed to transmit a first maximum force has a first connection element. A second force transmission element is designed to transmit a second maximum force greater than the first maximum force, the second force transmission element has a second connection element. The first grip has a coupling device for selectively force-fitting to the first or second connection elements of the first or second force transmission elements to the movable grip part. The first connection element has a first cross-section. The second connection element has a second cross-section different from the first cross-section. The coupling device has a first seat designed for a force-fit connection to the first connection element and a second seat designed for a force-fit connection to the second connection element.

18 Claims, 9 Drawing Sheets

DISMANTABLE MEDICAL FORCEPS SYSTEM

CROSS REFERENCE TO RELATED APPLICATION

The present application claims priority of German patent application No. 10 2007 658.2 filed on May 4, 2007.

BACKGROUND OF THE INVENTION

The invention generally relates to medical forceps systems comprising forceps which can be dismantled. More specifically, the invention relates to dismantlable forceps having a grip, a shaft, a force transmission element and a tool at the distal end.

A dismantlable medical forceps system known under the brand name CLICKline® is marketed by Karl Storz GmbH & Co. KG and is described, for example, in the company catalogue Storz Karl Storz-Endoskope, Laparoscopy Volume, 5th edition, 2005, pages 72 et seq.

Medical forceps are used in open surgery or in endoscopic surgery, for example for cutting, gripping, coagulating, etc., of tissue in the human or animal body.

Medical forceps generally have a grip with at least one movable grip part, an elongate shaft connected to the grip, at least one movable tool, for example jaw part, at the distal end of the shaft, and a force transmission element, usually in the form of a pull and push rod, which forms a force-fit connection between the at least one movable tool and the at least one movable grip part of the grip. By moving the at least one movable grip part, the force thereby generated is transmitted from the force trans-mission element to the at least one movable tool, in order to move the latter.

In order to permit better cleaning, medical forceps of this kind are designed such that they can be dismantled. The dismantlable forceps can usually be dismantled into the structural groups of grip, shaft and force transmission element, the at least one tool being connected as a structural unit to the force transmission element and being designated also as a working insert of the forceps.

The dismantlable nature of medical forceps not only increases the ease with which the forceps can be cleaned, it also increases the variability of function of such forceps, since different grips can be combined with different shafts and/or work inserts.

The known forceps system comprises, on the one hand, several different grips and, on the other hand, a plurality of different shafts and work inserts. Thus, the grips can differ in terms of the maximum force that can be generated, for example by providing grips whose at least one movable grip part can generate a high force because of a high lever action, while other grips are made smaller and generate a correspondingly lower force. A higher force is necessary, for example, for cutting or punching bone tissue, whereas a smaller handgrip is better suited for fine dissecting of softer tissue, because it permits better control of the force exerted by the physician's hand.

The force transmission elements too can differ in terms of the maximum force that can be transmitted by them. The maximum force that can be transmitted by the respective force transmission element is limited by the thickness of the force trans-mission element and of its connection element for connection to the movable grip part. For cutting bone tissue, a high force must be transmitted from the force trans-mission element to the at least one tool at the distal end, such that a force transmission element for these purposes has to be designed with a certain thickness, for example with a diameter of 3 mm. This also entails a correspondingly larger external diameter of the outer shaft through which the force transmission element extends between the grip and the at least one tool.

By contrast, in spatially confined surgery, for example in the ENT sector, very slender outer shafts of small diameter are needed, such that the force transmission element also has to be made relatively thin, for example with a diameter of approximately 1 mm.

To achieve the best possible compatibility, it is desirable that force transmission elements designed to transmit different maximum forces can be connected to one and the same grip, so as to minimize as far as possible the number of grips that have to be provided.

However, the known dismantlable forceps system mentioned above does not allow force transmission elements with different diameters to be received in one grip. Rather, the connection elements of the force transmission elements and of the coupling device of the grip or grips are of uniform design, with the result that each force transmission element can be connected only to one and the same grip. This leads, however, to the technical problems explained below, particularly when force transmission elements having very different thicknesses and, consequently, load-bearing capacities are intended to be combined in one forceps system.

When the work insert is preassembled, the force transmission element is pushed from the distal direction through the outer shaft. The connection element at the proximal end of the force transmission element is designed, for example, in the shape of a ball and also has to be able to pass through the outer shaft until it emerges from the proximal end of the outer shaft. If the force transmission element is designed to transmit a high force, the connection element also has to be designed with a suitable thickness in order to ensure that the connection between the force trans-mission element and the grip is able to withstand high forces. To allow the connection element of relatively large dimension to pass through the outer shaft, the outer shaft must have a relatively large diameter. Such a forceps system then has the disadvantage that, when the grip is connected to a thinner force transmission element, the outer shaft still has to have the same large diameter as in the case where a more strongly dimensioned force transmission element is connected to the grip, so as to ensure the compatibility between different force transmission elements and the same grip. Otherwise, a second grip with another coupling device would have to be made available, which is not consistent, however, with the objective of greater compatibility and undesirably increases the number of different grips.

Conversely, if the connection between the force transmission element and the grip is designed for the force transmission element permitting a low maximum force transmission, such that the connection element at the proximal end of the force transmission element can be made smaller, then, although the size of the outer shaft can be variable and in particular made thin, the maximum force that can be transmitted nevertheless remains limited to that of the smallest or weakest force transmission element. This means that when tools that require great force, for example bone punches, are used with a grip of suitably large dimension, breakage of the force transmission element in the area of the connection element cannot be ruled out when the grip is actuated with substantial manual force.

In this case, therefore, the physician operating the forceps has to carefully control the manual force exerted, so as to avoid breaking the force transmission element.

The known medical forceps system therefore has the disadvantage that the connection elements of the existing force transmission elements are intended for only one thickness, which results either in undesirably large external diameters of the outer shafts or in the risk of breakage of the force transmission element.

SUMMARY OF THE INVENTION

It is an object of the invention to develop a dismantlable medical forceps system such that force transmission elements with different force transmission properties can be connected to one and the same grip, without a minimum diameter of the outer shaft thus being required.

It is also an object of the invention to develop a dismantlable medical forceps system such that the danger of breakage of the force transmission element is reduced.

According to a first aspect of the invention, a dismantlable medical forceps system is provided, comprising at least one first grip having at least one movable grip part; a first force transmission element designed to transmit a first maximum force and having a first connection element; at least a second force transmission element designed to transmit a second maximum force greater than said first maximum force and having a second connection element; said at least one first grip having a coupling device for selectively connecting with a force fit one of said first or second connection elements of said first or second force transmission elements to said at least one movable grip part; said first connection element having a first cross section, said second connection element having a second cross section differing from said first cross section, said coupling device having a first seat designed for force-fit connection to said first connection element and at least a second seat designed for force-fit connection to said second connection element.

In accordance with this aspect, the dismantlable medical forceps system according to the invention thus has at least one grip to which at least two force transmission elements designed for different maximum force transmission can be alternately connected. For this purpose, the coupling device of this first grip is designed with at least two seats, one seat being designed for connecting the connection element of the first force transmission element to the grip with a force fit, and the at least one other seat being designed for connecting the connection element of the second force transmission element to the same grip with a force fit. In the dismantlable medical forceps system according to the invention, therefore, the number of grips that have to be provided can be reduced, since one and the same grip can be connected to different force transmission elements. This also means that a force transmission element which is designed for lower force transmission, and which is accordingly dimensioned with less thickness, can be connected together with a thinner shaft to the grip, and a more strongly dimensioned force transmission element which is designed for higher force transmission can be connected with a correspondingly larger shaft to the same grip. It will be appreciated that the coupling device can also have more than two seats for more than two differently designed force transmission elements.

According to a second aspect of the present invention, a dismantlable medical forceps system is provided, comprising a first grip having at least one movable first grip part and designed to generate a first maximum force, said first grip having a first coupling device; a first force transmission element having a first connection element for connection to said first coupling device; at least a second grip having at least one movable second grip part and designed to generate a second maximum force greater than said first maximum force that can be generated by said first grip, said second grip having a second coupling device; at least a second force transmission element having a second connection element for connection to said second coupling device; said first connection element having a first cross section, said second connection element having a second cross section different from said first cross section, said first coupling device having at least a first seat designed for force-fit connection to said first connection element, said second coupling device having a second seat for force-fit connection to said second connection element, said second seat being designed such that said first connection element cannot be connected with a force fit to said second seat.

In accordance with the present aspect comprising at least two different grips designed to generate different forces, the medical forceps system according to the invention thus has a coding property which ensures that a force transmission element designed for lower force transmission cannot be connected with a force fit to the grip designed for higher force transmission, as a result of which an "inadmissible" combination of force transmission element and grip is avoided. For this purpose, the first force transmission element and the second force transmission element each have connection elements that differ in terms of their cross section, and the coupling device of the second grip designed for the higher maximum force transmission does not permit a force-fit connection to the more weakly dimensioned force transmission element, thereby avoiding breakage of this force transmission element.

The term "seat" within the meaning of the present invention is to be understood generally and includes all configurations that permit a force-fit correction of the respective connection element to the seat.

In preferred embodiments of the dismantlable medical forceps system in accordance with both of the aforementioned aspects, the first and second cross sections of the first and second connection elements differ in terms of their cross-sectional shape and/or in terms of their cross-sectional size.

In the simplest case, and as is provided for in another preferred embodiment, the first connection element is spherical with a first diameter, and the second connection element is spherical with a second diameter larger than the first diameter.

The spherical shape of the connection elements has the advantage of being easier to produce, because the connection elements can be designed as lathed parts and in particular, in one working operation, can be made integral with the rest of the body of the respective force transmission element. In addition, the spherical shape of the connection elements means that, despite the force-fit connection, they can rotate in the respective seat about the longitudinal axis of the force transmission element, such that the tool, for example one or more jaw parts at the distal end of the instrument, can be turned relative to the grip part, as a result of which the position of the tool can be changed by the operator without modifying the position of the grip.

In another preferred embodiment of the dismantlable medical forceps system according to the first aspect, the first seat is at an axial distance from the second seat.

The advantage of this is that the possibility achieved according to the invention, namely that of being able to connect differently designed force transmission elements to the same grip, does not necessitate a greater transverse dimension of the coupling device and, therefore, of the grip in the area of the coupling device, because the at least two seats of the coupling device are arranged one behind the other in the longitudinal direction of the force transmission element.

In this context, it is preferable if the first connection element engages through the second seat when it is connected with a force fit to the first seat.

This embodiment is particularly suitable if the first and second connection elements differ in terms of their cross-sectional size. The connection element with the smaller cross-sectional size can then engage freely through the distal second seat designed for force-fit connection of the connection element of larger cross-sectional size, so as to be able to be connected with a force fit to the first proximal seat. In particular, this embodiment better permits the aforementioned advantage of a very slim coupling device structure.

In another preferred embodiment of the forceps system according to the first aspect, the coupling device has a coupling element which can move between a first position and a second position and which at least partially comprises the first and the at least second seat, the first or the at least second connection element being able to be introduced into or removed from the first or second seat in the first position, and the first or the at least second connection element being able to be locked in the first or second seat in the second position.

A corresponding embodiment is also preferably provided in the forceps system according to the second aspect.

The embodiment of the coupling device with a coupling element movable between an insertion position and a locking position has the advantage that the force-fit connection of the respective force transmission element to the grip can be done in a simple manoeuvre and, in particular if the coupling element is provided with a control mechanism, in a preferably automatic manner.

It is preferable if the coupling element can be moved by a rotation movement from the first position to the second position and vice versa, the coupling element being connected to an axially movable slide, which is connected to the movable grip part, and being axially immovable relative to the slide, and the rotation movement being derived from an axial movement of the slide.

By the coupling element being entrained in an axial movement of the slide upon force-fit connection of the first or second connection element to the coupling element, the coupling element is thus advantageously rotated automatically from the insertion position to the locking position and, when unlocked, in the reverse manner.

In another preferred embodiment, the first seat has a seat portion, in which the first connection element comes to lie when connected with a force fit, and a locking portion with a slit which engages over the force transmission element distally in front of the first connection element and has a width smaller than the maximum cross section of the first connection element.

It is also preferable, correspondingly, if the second seat has a seat portion, in which the second connection element comes to lie when connected with a force fit, and a locking portion with a slit which engages over the force transmission element distally in front of the second connection element and has a width smaller than the maximum cross section of the second connection element.

These aforementioned embodiments are of advantage in particular with the rotatable design of the aforementioned coupling element, because the force-fit connection between the first or second force transmission element and the first or second seat is very easy to obtain, namely in that the first or second connection element is initially introduced into the seat portion in the insertion position of the coupling device, after which the coupling element is rotated, for example by 90°, about a rotation axis extending perpendicular to the longitudinal direction of the respective force transmission element, as a result of which the edges of the respective slit engage over the respective force transmission element distally in front of the connection element thereof, in order to produce an especially stable and as far as possible clearance-free force-fit connection of the respective force transmission element in the respective seat.

In another preferred embodiment of the forceps system according to the first aspect, it comprises at least one second grip, which has at least one movable grip part, the at least one second grip having a second coupling device by means of which only the second force transmission element can be connected with a force fit to the movable grip part, while a force-fit connection to the first force transmission element is excluded.

This embodiment now has the particular advantage that the forceps system comprises one type of grips that allow differently dimensioned force transmission elements to be connected to the same grip, these grips being designed, in terms of the maximum force generated by them, such that the more weakly dimensioned force transmission element is not at risk of breaking, while the forceps system comprises at least one second type of grips that are designed for generating higher forces, and it is only more strongly dimensioned force transmission elements that can be connected with a force fit to the grips of this type. In this embodiment, therefore, the advantages of the abovementioned coding of force transmission elements for certain grips and the number of combination possibilities of different force transmission elements with one and the same grip are combined with one another in a forceps system.

In this context, it is also preferable if the second coupling device has a seat for the second connection element, said seat being designed such that the first connection element cannot be locked in the seat.

This measure has the advantage that, the first time the grip is actuated, the user senses that there is no force transmission from the grip to the tool, such that incorrect use is ruled out right from the start.

It is further preferable if the seat of the second coupling device is designed identically or substantially identically to the second seat of the first coupling device.

For example, the second coupling device can likewise be designed as a rotatable coupling element in which, in contrast to the coupling element of the first coupling device, only the second seat is present, while the first seat is missing in this coupling element. The advantage of this measure is that substantially the same parts can be used for the entire forceps system, only slight modifications being needed for the different functions, which reduces the production costs of the forceps system according to the invention.

Further advantages and features will become evident from the following description and from the attached drawing.

It will be appreciated that the aforementioned features and the features still to be explained below can be used not only in the respectively cited combination, but also in other combinations or singly, without departing from the scope of the present invention.

BRIEF DESCRIPTION OF THE DRAWINGS

Illustrative embodiments of the invention are described in more detail below with reference to the drawing, in which:

FIGS. 4a) and b) show a coupling device of the forceps from FIG. 2 on an enlarged scale and in longitudinal section, with a force transmission element introduced into the coupling device according to FIG. 4a) and locked therein according to FIG. 4b);

FIGS. 5a) and b)) are views corresponding to FIGS. 4a) and b) and show the connection of a further force transmission element to the coupling device in FIGS. 4a) and b);

FIGS. 8a) to c) are schematic plan views of the coupling device from FIGS. 4, 5 and 6, illustrating a control mechanism for transferring the coupling element from an insertion position according to FIG. 8a) to a locking position according to FIG. 8c).

DETAILED DESCRIPTION OF PREFERRED EXEMPLARY EMBODIMENTS

Figure 1A:
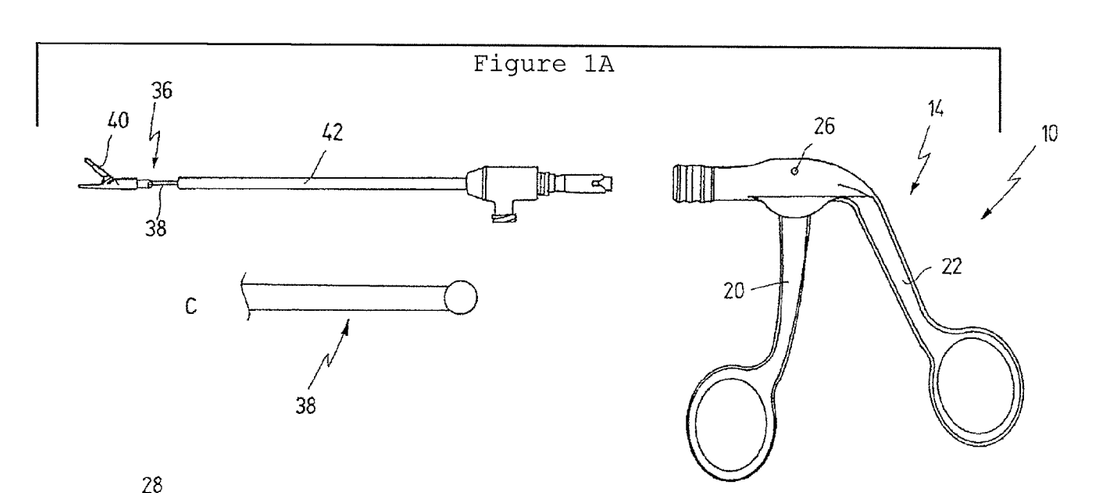
FIG. 1A shows a dismantlable medical forceps system being shown by way of example in the dismantled state.
Figure 1B:
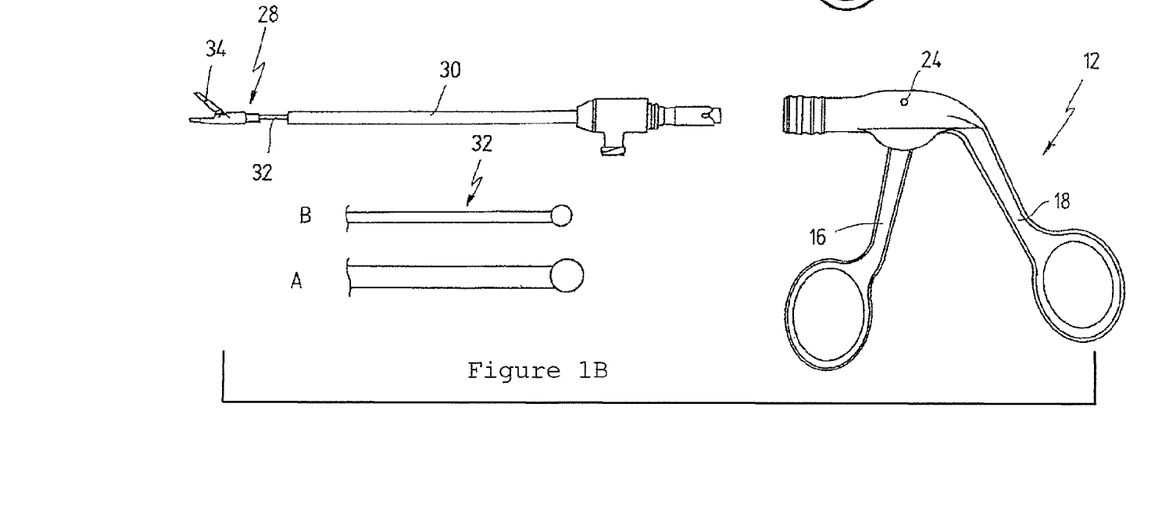
FIG. 1B shows a dismantlable medical forceps system being shown by way of example in the dismantled state.

In FIGS. 1A and 1B, a dismantlable medical forceps system is designated overall by reference number 10. Without implying any limitation, the forceps system 10 is used in ear, nose and throat medicine and surgery.

The forceps system 10 has a first grip 12 and a second grip 14. The first grip 12 has a first movable grip part 16 and a first immovable grip part 18. Likewise, the second grip part 414 has a second movable grip part 20 and a second immovable grip part 22.

The first grip 12 is designed to generate a maximum force that is smaller than the maximum force that can be generated with the second grip 14. In the illustrative embodiment shown, this is achieved by the fact that the first movable grip part 16 of the first grip 12 has a smaller lever length, relative to a first pivot axis 24, than does the second movable grip part 20 relative to a second pivot axis 26.

FIGS. 1A and 1B also shows an example of a first work insert 28 and a shaft 30, the arrangement composed of the work insert 28 and of the shaft 30 being able to be connected to the first grip 12, although the work insert 28 and the shaft 30 are shown detached from the grip 12 in FIGS. 1A and 1B. The first work insert 28 has a first force transmission element 32 which at one end is connected distally to a movable tool 34, which is designed for example as a cutting, punching or gripping jaw part. The force transmission element 32 is designed in the form of a pull/push rod. A proximal end of the force transmission element 32, not shown in FIGS. 1A and 1B, serves for force-fit connection to the first grip 12, or to be more exact to the first movable grip part 16, such that a movement of the first movable grip part 16 is converted into an axial movement of the first force transmission element 32, the latter moving the distal tool 34. In FIGS. 1A and 1B, the first work insert 28 is released from the shaft 30 and is shown protruding slightly distally from the shaft 30, such that the proximal end of the first force transmission element 32 cannot be seen in FIGS. 1A and 1B.

FIGS. 1A and 1B also shows a second work insert 36 with a second force transmission element 38, a second distal movable tool 40 and a second shaft 42.

The first force transmission element 32, which can be connected with a force fit to the first grip 12, can be one that is designed to transmit a high maximum force, as is shown schematically and on an enlarged scale in the detail A in FIG. 1A, or it can be a force transmission element designed to transmit a low maximum force, as is shown in the detail B in FIG. 1A. Accordingly, the force transmission element shown in detail B is designed with a lesser thickness than the force transmission element shown in detail A.

By contrast, the second grip 14, designed to generate greater forces, can be connected with a force fit only to a force transmission element 38 that is designed to transmit high forces, as is shown in detail C in FIG. 1B, which corresponds to detail A in FIG. 1A.

In the description below, the first force transmission element 32 is described as one that is designed to transmit a low maximum force, and the second force transmission element 38 is described as one that is designed to transmit a high maximum force, which is thus greater than the maximum force that can be transmitted by the first force transmission element 32.

Figure 2:
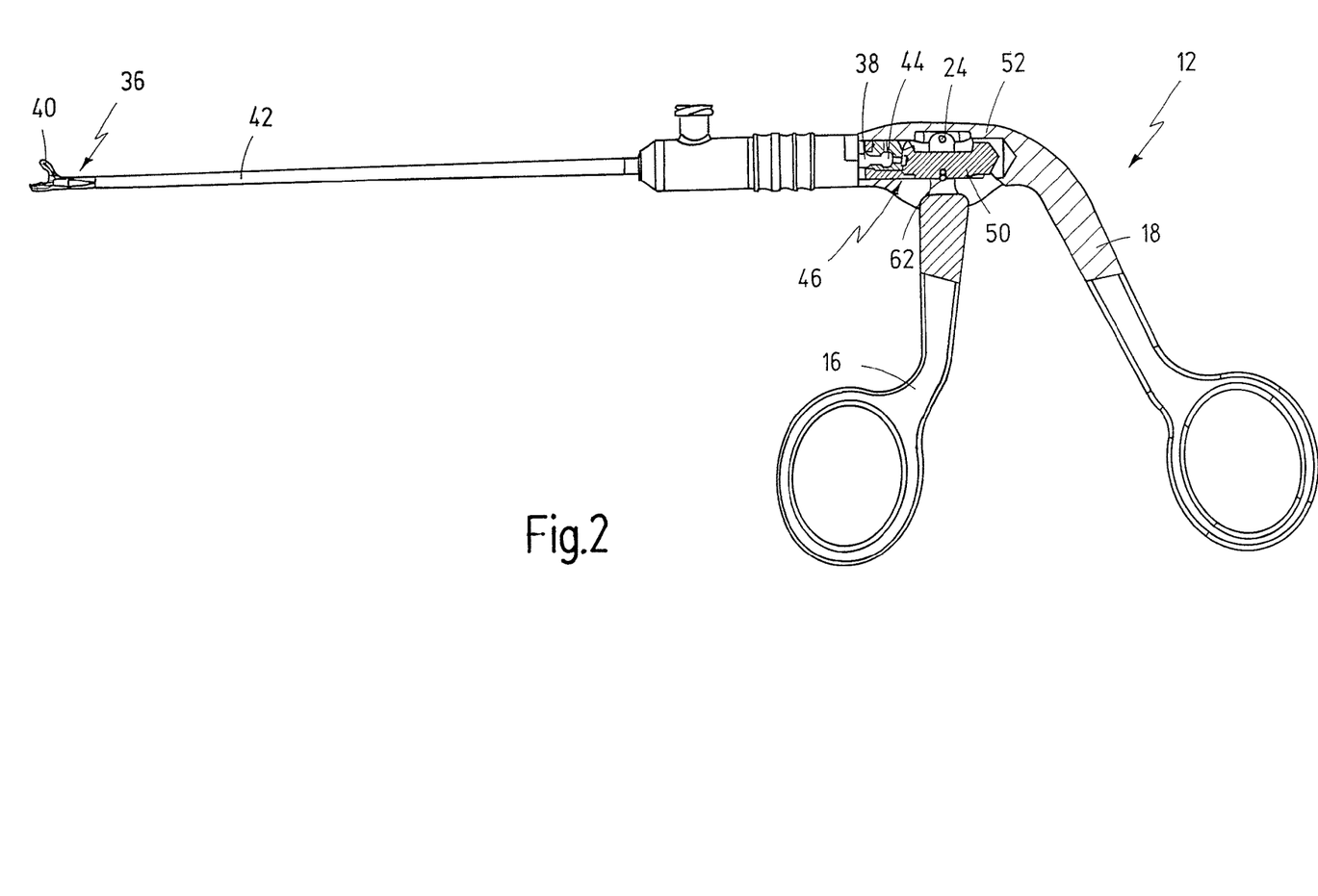
FIG. 2 shows one of the two forceps from FIG. 1 in the assembled state, partially in longitudinal section.

FIG. 2 shows forceps composed of the first grip 12 and of the second shaft 42 together with the second work insert 36 and distal tool 40 and including force transmission element 38. At its proximal end, the force transmission element 38 has a second connection element 44 of spherical design. According to the sectional view in FIG. 2, the grip 12 has a coupling device 46 for force-fit connection of the force transmission element 38 to the grip 12, more exactly to the movable grip part 16. In the state shown in FIG. 2, the connection element 44 is locked onto the first coupling device, such that the forceps shown in FIG. 2 are ready for use.

Figure 3:
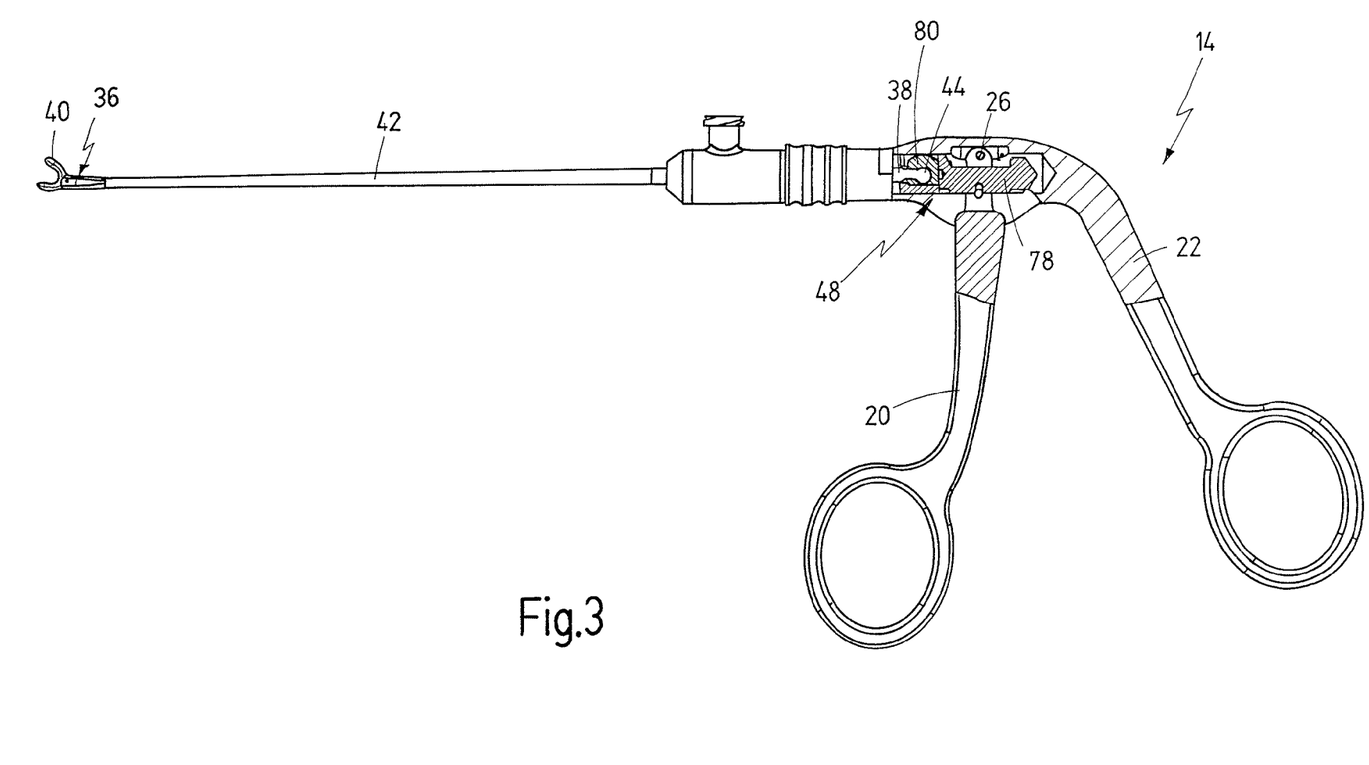
FIG. 3 shows the other of the two forceps from FIG. 1 in the assembled state, partially in longitudinal section.

FIG. 3 shows, in the same schematic depiction as in FIG. 2, forceps composed of the grip 14 and of the work insert 36 with shaft 42 and force transmission element 38, said grip 14 having a coupling device 48, which will be described in more detail below.

First, the coupling device 46 will be described in detail with reference to FIGS. 2 and 4a) and b).

The coupling device 46 has a slide 50 which is axially movable in a grip housing 52 of the grip 12, i.e. in the longitudinal direction of the shaft 42 or of the force trans-mission element 38. The coupling device 46 also comprises a coupling element 54, which is arranged in a blind-hole seat 56 of the slide 50, the first coupling element 54 being axially immovable relative to the slide 50 but being able to move in rotation in the blind-hole seat 56 about an axis 58 that extends perpendicular to the longitudinal direction of the force transmission element 38.

Figure 7:
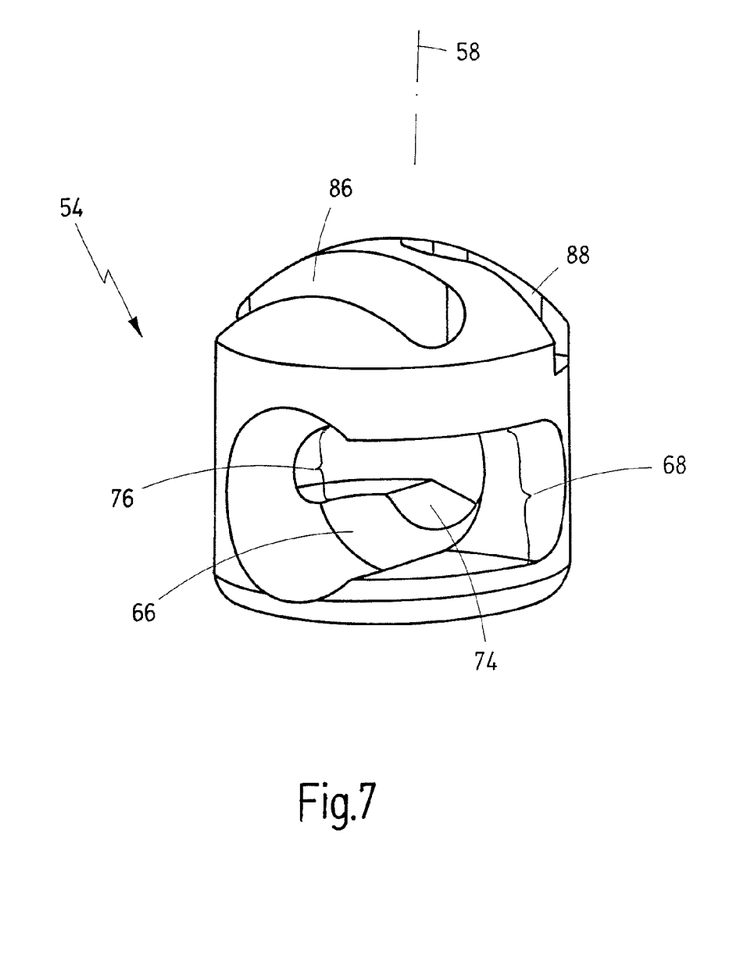
FIG. 7 shows a coupling element of the coupling device from FIGS. 4 and 5 in a perspective view and on a further enlarged scale.

The first coupling element 54 is shown on its own, and enlarged, in FIG. 7.

She slide 50 has a recess 60 into which a driver pin 62 of the first movable grip part 16 engages, such that, when the first movable grip part 16 is pivoted about the pivot axis 24, the slide 50 is moved axially in the distal or proximal direction, depending on the direction of pivoting of the grip part 16.

The coupling element 54 has a seat 64 which is formed as a recess in the coupling element 54 and which is used for force-fit connection of the connection element 44 of the force transmission element 38. The seat 64 is for this purpose substantially spherical in cross section, such that the spherical connection element 44 can be received with a form fit in the seat 64.

Figure 4:
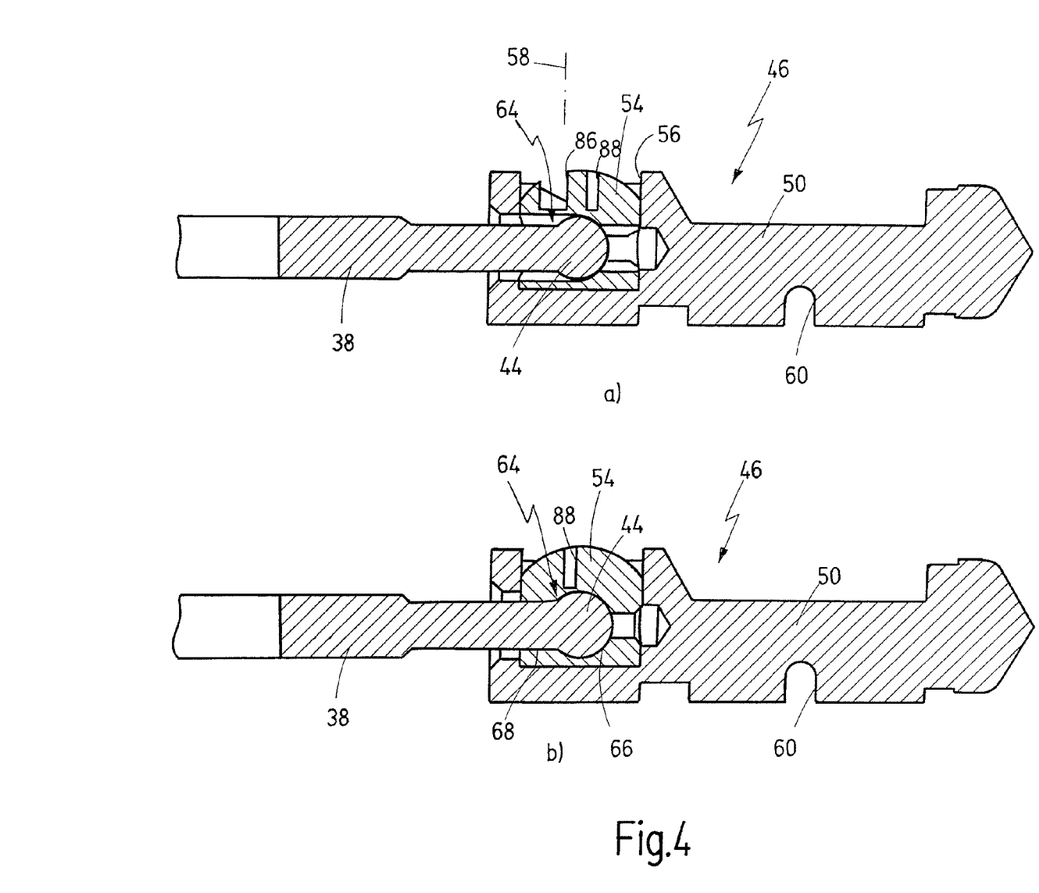

The seat 64 more specifically comprises a seat portion 66 in which the second connection element 44 comes to lie when connected with a force fit, and a locking portion 68 with a slit which engages over the force transmission element 38 distally in front of the connection element 44 and has a width that is smaller than the maximum cross section of the connection element 44, as will be seen from FIG. 4*b*). As is shown in FIG. 7, the locking portion 68 extends in the circumferential direction about the rotation axis 58 laterally away from the seat portion 66. In this configuration, there is a form-fit engagement between the connection element 44 and the seat 64 in the locked state.

The coupling element 54 in the blind-hole seat 56 can be rotated about the rotation axis 58 by approximately 90°, this rotation also being able to correspond to another angle, specifically between a first position (insertion position), which is shown in FIG. 4*a*), and a second position (locking position), which is shown in FIG. 4*b*). In the position of the coupling element 54 shown in FIG. 4*b*), the force transmission element 38 is connected with a force fit to the coupling device 46 and thus to the grip 12 or the movable grip part 16.

The way in which the rotation movement of the coupling element 54 is derived from an axial movement of the slide 50 will be described later.

Figure 5:
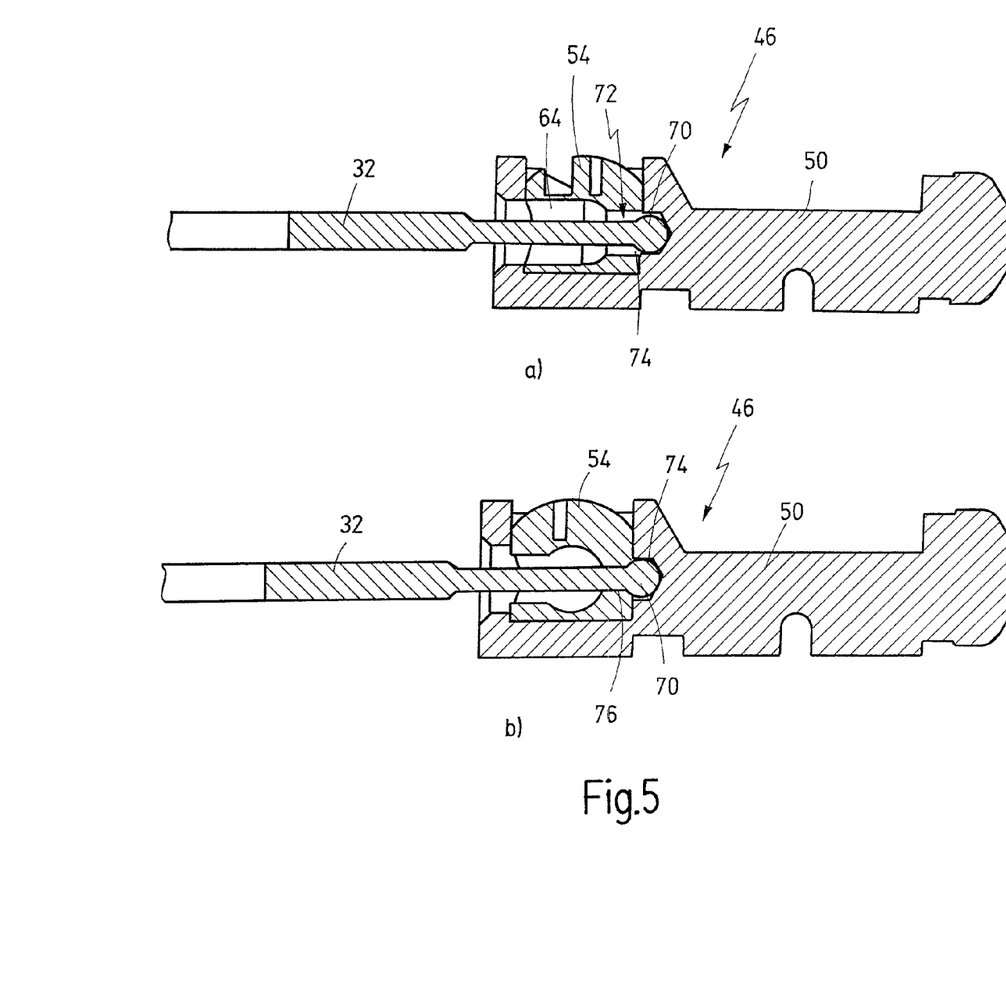

FIGS. 5*a*) and *b*) now show that, in addition to the force transmission element 38 designed to transmit a high force being able to be connected with a force fit to the coupling device 46, the force transmission element 32 designed to transmit a smaller maximum force can also be connected to it with a force fit.

Compared to the force transmission element 38, the force transmission element 32 has an overall lesser thickness and has, at its proximal end, a connection element 70 which, although spherical like the second connection element 44, differs from the latter in terms of its cross-sectional size, i.e. is smaller.

Figure 9:
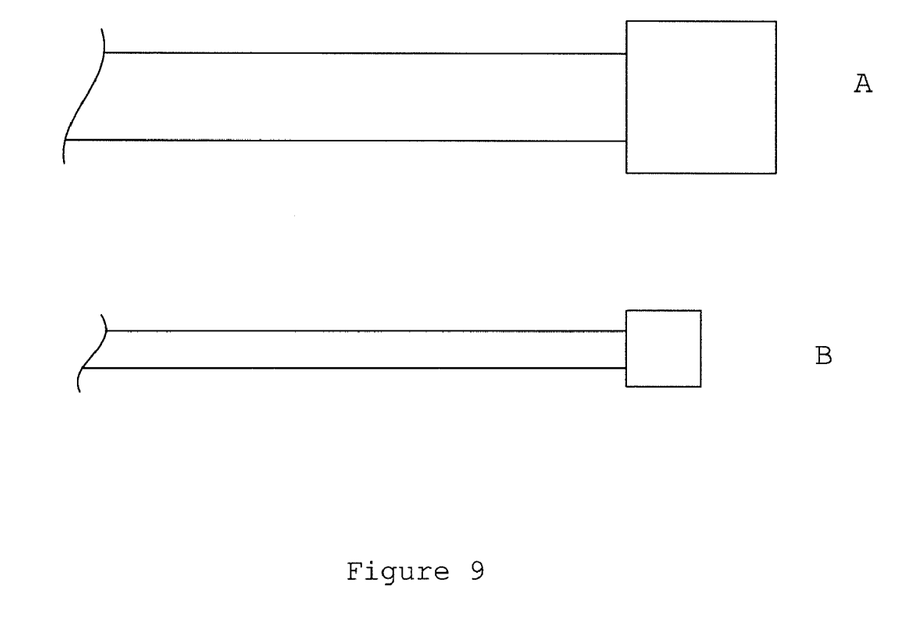
FIG. 9 shows a connection element having a different cross-sectional shape from the connection elements of FIG. 1.

In a departure from the illustrative embodiment shown, however, it is also possible that the connection element 70 and the connection element 44 do not differ, or do not only differ, in terms of their cross-sectional size, and instead configurations are also possible in which the connection elements 70 and 44 differ in terms of their cross-sectional shape. (See A and B of FIG. 9). Instead of being spherical, the first connection element 70, for example, can be cuboid, cylindrical or flat, to mention but a few examples.

For the first connection element 70, the coupling device 46 has a seat 72 that is at an axial distance from the seat 64, the seat 72 being arranged in the proximal direction from the seat 64.

The seat 72 again has a seat portion 74 which, in the illustrative embodiment shown, is formed also partially in the slide 50. However, the seat portion 74 can also be arranged completely in the coupling element 54.

The seat 72 furthermore comprises a locking portion 76 with a slit that engages over the force transmission element 32 distally in front of the connection element 70 and has a width smaller than the maximum cross section of the connection element 70. According to FIG. 7, the locking portion 76 extends in the circumferential direction about the rotation axis 58 laterally from the seat portion 74, specifically in the same sense of rotation as the locking portion 68 of the seat 64. FIG. 5*a*) shows the coupling element 54 again in the insertion position, in which the force transmission element 32, with the connection element 70 at the front, can be inserted into the seat 72 or can be removed from the latter, and FIG. 5*b*) shows the coupling element 54 in a locking position, which is rotated by 90° about the rotation axis 58 relative to the insertion position and in which the force transmission element 32 is connected with a force fit to the coupling device 46.

The connection element 70 engages through the seat 64 when it is connected to the seat 72. For this purpose, the seat 64 is accordingly designed with a suitably large cross section. The length of the force transmission elements 32 and 38 is preferably different, such that, independently of the force transmission element 32 or 38 used, the tool 34 or 40 at the distal end is located at the same distance from the grip 12.

Thus, the force transmission element 32 or the force transmission element 38 can alternately be connected with a force fit to the grip 12. Since the grip 12 can only generate a maximum force that the force transmission element 32 is able to withstand, there is no danger or only minimal danger of breakage if the "weaker" force transmission element 32 is connected to the grip 12.

By contrast, as will be described below, the grip 14, which is designed to transmit higher forces, can be connected with a force fit only to the second force transmission element 38, whereas the first force transmission element 32 cannot be connected with a force fit to the second grip 14.

Figure 6:
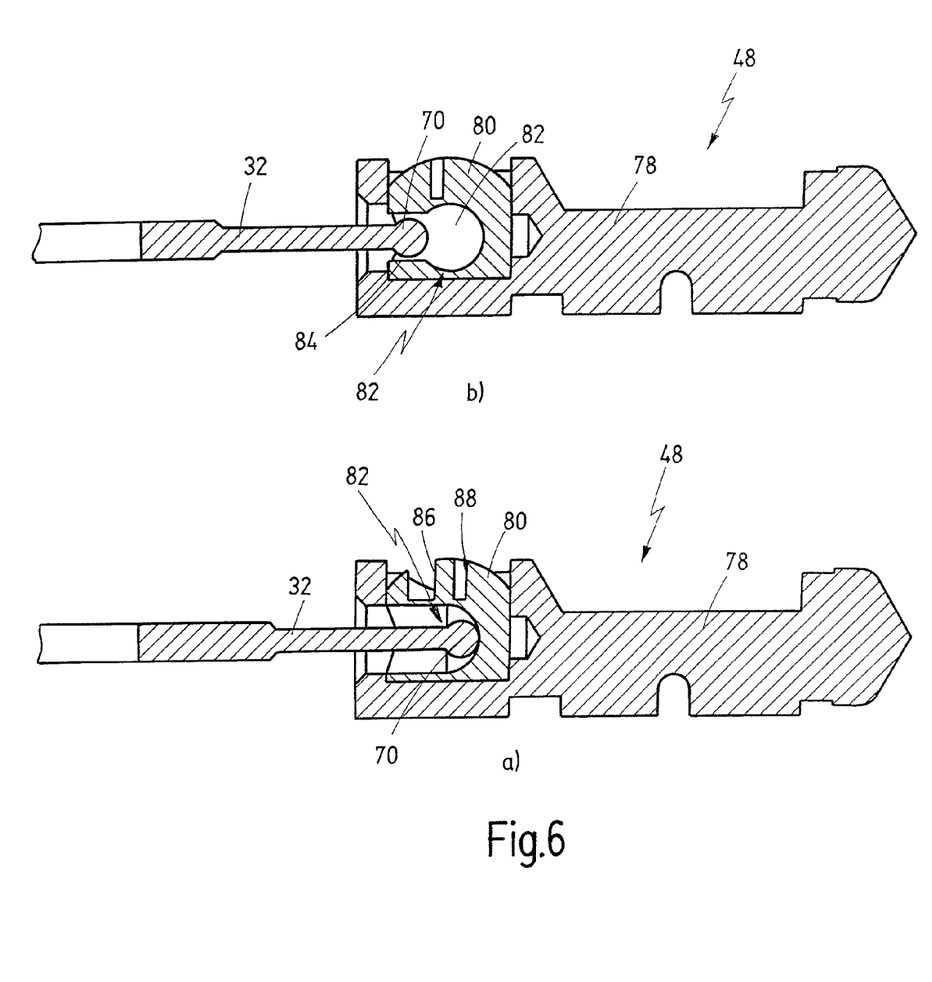
FIG. 6 shows a coupling device of the forceps from FIG. 3 on an enlarged scale and in longitudinal section, FIG. 6a) showing the force transmission element according to FIG. 4a) introduced into the coupling device, and FIG. 6b) showing that this first force transmission element cannot be connected with a force fit to this coupling device.

According to FIGS. 3 and 6*a*) and *b*), the coupling device 48 has a slide 78, which is preferably identical in design to the slide 50 of the coupling device 46, which reduces the manufacturing costs, since at least partially identical structural parts can be used for the grip 12 and the grip 14. The function of the slide 78 is also identical to the function of the slide 50 as has been described above.

The coupling device 48 furthermore comprises a coupling element 80, which is also identical to the coupling element 54, except for the following features. In contrast to the coupling element 54, the coupling element 80 has only one seat 82, which is of a design identical to the seat 64 of the coupling element 54. By contrast, the coupling element 80 does not have the seat 72 of the coupling element 54. This has the effect that although the connection element 70 of the force transmission element 32, in the insertion position of the coupling element 80 shown in FIG. 6*a*), can be introduced into the seat 82, when the coupling element 80 is rotated in its locking position according to FIG. 6*b*), no force-fit connection is established between the connection element 70 and the seat 82, because the connection element 70 has a smaller cross section than the locking portion 84 of the seat 82.

There is therefore no possibility of a user connecting the more weakly dimensioned force transmission element 32 to the more strongly dimensioned second grip 14, as a result of which breakage of the force transmission element 32 is ruled out in each case. The grip 14 thus has a coding property that permits only a force-fit connection of the more strongly dimensioned force transmission element 38 to the grip 14 and does not permit a force-fit connection of the more weakly dimensioned force trans-mission element 32 to the grip 14.

Figure 8:
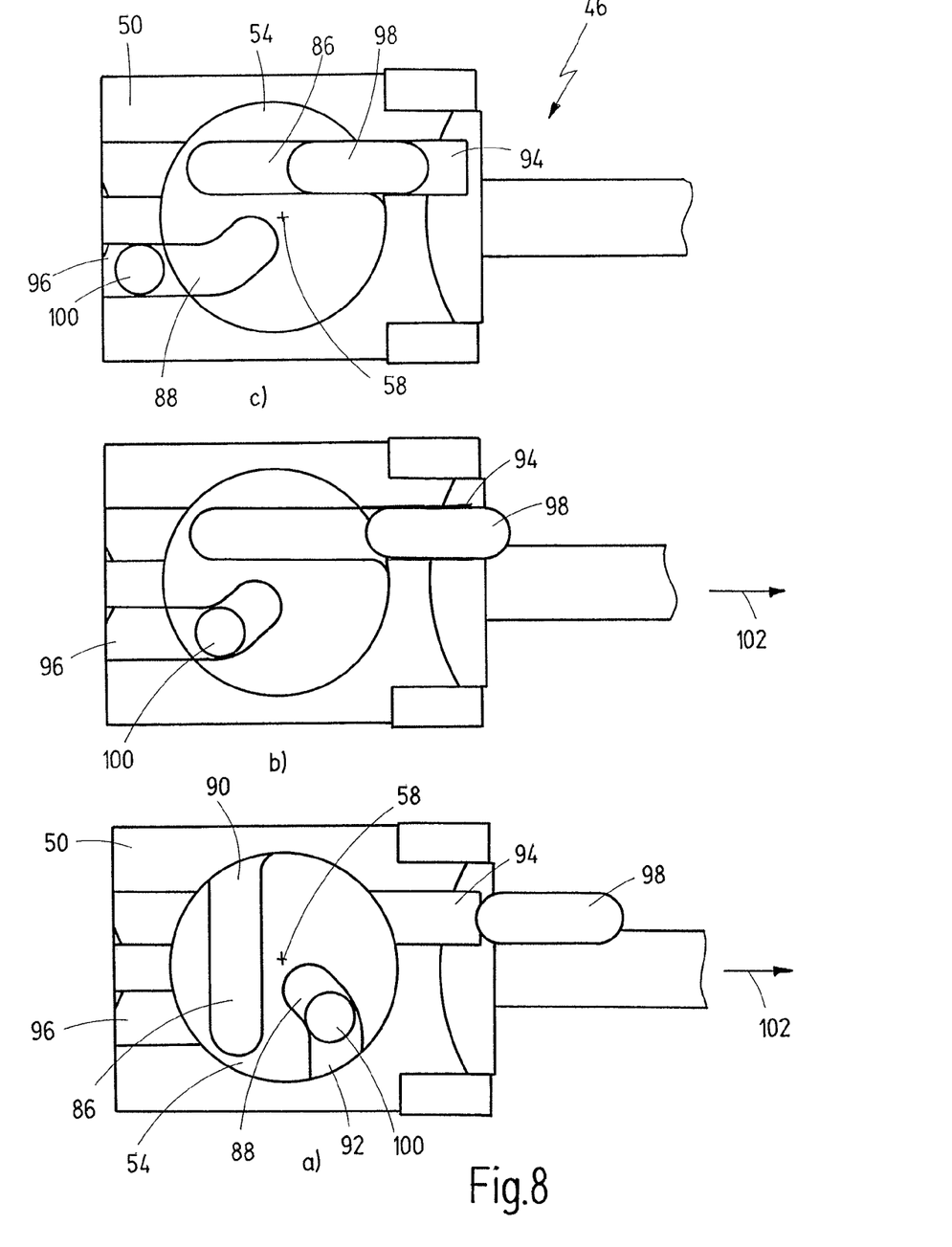

Both the coupling element 54 and the coupling element 80 derive their rotation movement between insertion position and locking position from an axial movement of the slide 50 or 78, as will be described below with reference to the schematic drawings in FIGS. 8*a*) to *c*) depicting the coupling device 46 of the grip 12. FIGS. 8*a*) to *c*) are plan views of the slide 50 and the coupling element 54.

The coupling element 54 has a first control cam 86 designed in the form of seat shaped as an oblong hole, as can also be seen in FIG. 7. The coupling element 54 furthermore comprises a second control cam 88, which is likewise designed as a recess in the form of an oblong hole, but which has a curved profile in contrast to the first control cam 86. The first control cam 86 is open at one end 90, and the second control cam 88 is open at one end 92, said ends 90 and 92 being offset by approximately 180° relative to the rotation axis 58, which extends perpendicular to the plane of the drawing in FIGS. 8 *a*) to *c*).

The slide 50 has two recesses 94 and 96.

To control the rotation movement of the coupling element 54 derived from the axial movement of the slide 50, two guide elements 98 and 100 are provided, which are immovable and are secured, for example, on the inside of the grip housing 52.

FIG. 8*a*) shows the coupling element 54 in its insertion position, in which the force transmission element 32 or the force transmission element 38, with its respective connection element 44 or 70 at the front, can be inserted into the respective first or second seat described above. The guide element 100 is in engagement with the second control cam 88 in this position.

When, starting from FIG. 8*a*), the slide 50 is moved axially in the direction of an arrow 102, the guide element 100, which engages in the second control cam 88, causes a 90° rotation of the coupling element 54 relative to the slide 50, on account of the curved configuration of the second control cam 88. Meanwhile, the guide element 98 moves initially into the recess 94 of the slide 50.

Upon a further axial movement of the slide 50 in the direction of the arrow 102, the guide element 100 now disengages from the second control cam 88, and the guide element 98 moves partially into the first control cam 86, but also remains partially in the recess 94 of the slide 50, as a result of which the coupling element 54 is locked in a rotationally fixed manner to the slide 50. The force transmission element 32 or 38 is now connected with a force fit to the coupling device 46. The dismantling is accordingly carried out in the reverse manner.

When the forceps described above are in the state ready for use, the axial mobility of the slide 50 is limited by a limit stop, which is formed by a proximal shaft edge. It is only when the shaft 42, for example, is released from the handgrip 12 (see FIGS. 1A and 1B and FIG. 2) that the slide 50 can be moved axially beyond its axial stroke necessary for actuating the tool 34, for example, in order to allow the force transmission element 32 or 38 to be connected to or separated from the coupling device 46.

What is claimed is:

1. A dismantlable medical forceps system, comprising:
    at least one first grip having at least one movable grip part;
    a first force transmission element designed to transmit a first maximum force and having a first connection element;
    at least a second force transmission element designed to transmit a second maximum force greater than said first maximum force and having a second connection element;
    said at least one first grip having a coupling device for selectively connecting with a force fit one of said first or second connection elements of said first or second force transmission elements to said at least one movable grip part;
    said first connection element having a first cross section, said second connection element having a second cross section differing from said first cross section, said coupling device having a first seat designed for force-fit connection to said first connection element and at least a second seat designed for force-fit connection to said second connection element;
    wherein said first and second cross sections are perpendicular to a longitudinal direction of said first and said second force transmission elements, and
    wherein said first and second cross sections of said first and second connection elements differ in terms of a cross-sectional shape.

2. The forceps system of claim 1, wherein said first seat is at an axial distance from said second seat.

3. The forceps system of claim 2, wherein said first connection element engages through said second seat when it is connected with a force fit to said first seat.

4. The forceps system of claim 1, wherein said coupling device has a coupling element which can move between a first position and a second position and which at least partially comprises said first seat and said at least second seat, said first or said at least second connection element being able to be introduced into or removed from said first or second seat in said first position, and said first or said at least second connection element being able to be locked in said first or second seat in said second position.

5. The forceps system of claim 4, wherein said coupling element can be moved by a rotation movement from said first position to said second position and vice versa, wherein said coupling element is connected to an axially movable slide, which is connected to said movable grip part, and is axially immovable relative to said slide, and wherein said rotation movement is derived from an axial movement of said slide.

6. The forceps system of claim 1, wherein said first seat has a seat portion, in which said first connection element comes to lie when connected with a force fit, and a locking portion with a slit which engages over said first force trans-mission element distally in front of said first connection element and has a width smaller than a maximum cross section of said first connection element.

7. The forceps system of claim 1, wherein said second seat has a seat portion, in which said second connection element comes to lie when connected with the force fit, and a locking portion with a slit which engages over said second force transmission element distally in front of said second connection element and has a width smaller than a maximum cross section of said second connection element.

8. The forceps system of claim 1, further comprising at least one second grip, which has at least one second movable grip part, wherein said at least one second grip has a second coupling device, wherein only the second force trans-mission element can be connected with a force fit to said second movable grip part, while a force-fit connection to said first force transmission element is excluded.

9. The forceps system of claim 8, wherein said second coupling device has a seat for said second connection element, said seat being designed such that said first connection element cannot be locked in said seat.

10. The forceps system of claim 9, wherein said seat of said second coupling device is designed substantially identically to said second seat of said first coupling device.

11. The forceps system of claim 1, wherein said first connection element is spherical with a first diameter, and a second connection element is spherical with a second diameter greater than said first diameter.

12. A dismantlable medical forceps system, comprising:
    a first grip having at least one movable first grip part and designed to generate a first maximum force, said first grip having a first coupling device;
    a first force transmission element having a first connection element for connection to said first coupling device;
    at least a second grip having at least one movable second grip part and designed to generate a second maximum force greater than said first maximum force that can be generated by said first grip, said second grip having a second coupling device;

at least a second force transmission element having a second connection element for selective connection to said second coupling device and for selective connection to said first coupling device;

said first connection element having a first cross section, said second connection element having a second cross section different from said first cross section, said first coupling device having at least a first seat designed for force-fit connection to said first connection element, said second coupling device having a second seat for force-fit connection to said second connection element, said second seat being designed such that said first connection element cannot be connected with a force fit to said second seat;

wherein said first and second cross sections are perpendicular to a longitudinal direction of said first and said second force transmission elements.

13. The forceps system of claim 12, wherein said first and second cross sections of said first and second connection elements differ in terms of a cross-sectional shape.

14. The forceps system of claim 12, wherein said first and second cross sections of said first and second connection elements differ in terms of a cross-sectional size.

15. The forceps system of claim 12, wherein said second coupling device has a coupling element which can move between a first position and a second position and which has said second seat, said second connection element being able to be introduced into or removed from said second seat in said first position, and said second connection element being able to be locked in said second seat in said second position.

16. The forceps system of claim 15, wherein said coupling element can be moved by a rotation movement from said first position to said second position and vice versa, wherein said coupling element is connected to an axially movable slide, which is connected to said movable grip part, and is axially immovable relative to said slide, and wherein said rotation movement is derived from an axial movement of said slide.

17. The forceps system of claim 12, wherein said second seat has a seat portion in which said second connection element comes to lie when connected with a force fit, and a locking portion with a slit which engages over said second force transmission element distally in front of said second connection element and has a width smaller than a maximum cross section of said second connection element, but greater than a maximum cross section of said first connection element.

18. A dismantlable medical forceps system, comprising:
at least one first grip having at least one movable grip part;
a first force transmission element designed to transmit a first maximum force and having a first connection element;
at least a second force transmission element designed to transmit a second maximum force greater than said first maximum force and having a second connection element;
said at least one first grip having a coupling device for selectively connecting with a force fit one of said first or second connection elements of said first or second force transmission elements to said at least one movable grip part;
said first connection element having a first cross section, said second connection element having a second cross section differing from said first cross section, said coupling device having a first seat designed for force-fit connection to said first connection element and at least a second seat designed for force-fit connection to said second connection element;
wherein said first and second cross sections are perpendicular to a longitudinal direction of said first and said second force transmission elements, and
wherein said first and second cross sections of said first and second connection elements differ in terms of a cross-sectional size.

* * * * *